United States Patent
Shibuya

[11] Patent Number: 5,876,441
[45] Date of Patent: Mar. 2, 1999

[54] INTRAOCULAR LENS WITH A PRESS STRETCHED PORTION

[75] Inventor: Akihiko Shibuya, Tokyo, Japan

[73] Assignee: Hoya Corporation, Japan

[21] Appl. No.: 815,709

[22] Filed: Mar. 12, 1997

[30] Foreign Application Priority Data

Mar. 19, 1996 [JP] Japan .................................. 8-062674

[51] Int. Cl.⁶ .................................................. A61F 2/16
[52] U.S. Cl. ............................................................ 623/6
[58] Field of Search ...................................... 623/6

[56] References Cited

U.S. PATENT DOCUMENTS

| | | | |
|---|---|---|---|
| 4,361,527 | 11/1982 | Rau | 264/25 |
| 4,732,715 | 3/1988 | Bawa et al. | 264/1.4 |
| 4,815,690 | 3/1989 | Shepherd | 623/6 |
| 5,169,569 | 12/1992 | Ingram et al. | |
| 5,269,813 | 12/1993 | Yoshida et al. | 623/6 |
| 5,674,284 | 10/1997 | Chang et al. | 623/6 |
| 5,725,574 | 3/1998 | Nguyen | 623/6 |

FOREIGN PATENT DOCUMENTS

| | | |
|---|---|---|
| 4-212349 | 8/1992 | Japan . |
| 7-144000 | 6/1995 | Japan . |
| WO 94/04346 | 3/1994 | WIPO . |

*Primary Examiner*—Paul B. Prebilic
*Attorney, Agent, or Firm*—Nixon & Vanderhye

[57] ABSTRACT

A one-piece intraocular lens made entirely of three-dimensionally crosslinked polymethyl methacrylate is described. The lens is made from a lens blank which is selectively press-stretched in those areas around the periphery of the central effective optic area and from which the haptic portions are formed rendering areas more robust and less prone to fracture while the central effective optic area is not press-stretched. The lenses are durable to YAG laser irradiation.

4 Claims, 2 Drawing Sheets

INTRAOCULAR LENS WITH A PRESS STRETCHED PORTION

FIELD OF THE INVENTION

The present invention relates to an intraocular lens and a process for the production thereof, particularly to an intraocular lens of which the optic and hepatic portions are integrated and a process for the production thereof.

PRIOR ART

An intraocular lens includes a two-piece intraocular lens (or sometimes called a three-piece intraocular lens) of which the haptic and optic portions are separately produced and combined, and a one-piece intraocular lens of which the haptic and optic portions are integrated.

Most of two-piece or three-piece intraocular lenses are composed of a haptic portion formed of polypropylene (PP) and an optic portion formed of polymethyl methacrylate or methyl methacrylate copolymer (these will be generically referred to as "PMMA" in the present specification). In most of one-piece intraocular lens, the haptic portion and the optic portion are formed of PMMA.

With an advance in mechanical processing, the main stream of the above intraocular lenses is shifting from two-piece intraocular lenses to one-piece intraocular lenses.

The reason for the use of PMMA for an intraocular lens is that PMMA is excellent in bio-compatibility, mechanical processability and transparency. Due to these advantages, PMMA is very useful for an intraocular lens which is to be implanted in the eye.

On the other hand, PMMA has the mechanical properties of being hard and fragile. An integral intraocular lens formed of PMMA therefore has a problem that the haptic portion is liable to break under a load exerted on the haptic portion at the time of an implanting operation.

For overcoming the above problem, there is employed a method in which a PMMA sheet is stretched to improve its strength. One method is that a PMMA sheet is multi-axially stretched under heat. In this method, facing margins of a PMMA sheet are clamped with a tool, the PMMA sheet is uniformly heated and the PMMA sheet is simultaneously stretched in directions of multiple axes to stretch and orient the PMMA sheet. When the above stretched PMMA sheet is used, there can be produced an intraocular lens of which the haptic and optic portions are integrated and the haptic portion is free from breaking. This above method is disclosed, for example, in JP-A-4--212349.

Further, a PMMA sheet may also be stretched by another method using blow stretching. In this method, the principle of stretch blow molding typically used for producing foods- and medicine-related containers. A PMMA sheet which is heat-plasticized is expanded to stretch and orient it by blowing in a hot fluid (air is usual). This above method is disclosed, for example, in U.S. Pat. No. 5,169,569.

Further, since the above methods or procedures of stretching a PMMA sheet are difficult, there is another method in which a PMMA sheet (having the form of a button) is press-stretched with a compression molding machine to improve PMMA in mechanical strength. This method is disclosed, for example, in JP-A-7-144000 and WO94/04346.

As another material for an intraocular lens, there is a three-dimensionally crosslinked PMMA in addition to the PMMA. The three-dimensionally crosslinked PMMA refers to a network PMMA polymer obtained by reacting dimethacrylate of a polyhydric alcohol such as ethylene glycol dimethacrylate as a crosslinking agent when PMMA is produced by polymerization. The network PMMA polymer is clearly distinguishable from a conventional linear PMMA polymer. The three-dimensionally crosslinked PMMA has excellent in stability as a substance and excellent durability against irradiation by a YAG laser. For the therapeutic treatment of adult cataract, a diseased portion is irradiated with YAG laser through an intraocular lens. When the intraocular lens formed of general PMMA, the optic portion may undergo cracking, while the three-dimensionally crosslinked PMMA does not cause such cracking.

The three-dimensionally crosslinked PMMA is advantageous as described above when used as a material for an intraocular lens. In conventional stretching methods disclosed in the above publications, three-dimensionally crosslinked PMMA is not used as a material. That is because it is difficult to stretch the three-dimensionally crosslinked PMMA since it has low thermoplasticity as compared with general linear PMMA. Further, since it has a crosslinked structure, it is considered difficult to improve the strength even if it is stretched.

SUMMARY OF THE INVENTION

The present invention overcomes the above problems, and it is an object of the present invention to provide an integral intraocular lens which retains the features of three-dimensionally crosslinked PMMA excellent in physico-chemical stability and YAG laser durability, and which is improved in the strength of the haptic portion so that the haptic portion has improved breaking resistance.

The present inventor has found the following.

(1) A three-dimensionally crosslinked PMMA can be press-stretched by properly controlling the degree of crosslinking.

(2) Having an effective optic area composed of a three-dimensionally crosslinked PMMA which has an appropriate crosslinking degree but is not pressed or stretched, and a peripheral portion to the effective optic area and a haptic portion composed of a three-dimensionally crosslinked PMMA which has an appropriate degree of crosslinking and is press-stretched, an integral intraocular lens has excellent physicochemical stability and YAG laser durability. Further, the haptic portion is improved in mechanical strength and is improved in breaking resistance.

(3) The intraocular lens having the constitution described in the above (2) can be obtained by polymerizing a monomer mixture of methyl methacrylate with a specific amount of a crosslinking agent to obtain a three-dimensionally crosslinked PMMA having an appropriate degree of crosslinking; press-stretching the obtained PMMA under heat with a press plate having a hole having a diameter equal to, or greater than, the diameter of the effective optic area and equal to, or smaller than, the outer diameter of the peripheral portion until a press-stretched portion has a predetermined thickness; and subjecting the resultant product to predetermined mechanical processing.

DETAILED DESCRIPTION OF THE INVENTION

Figure 1:
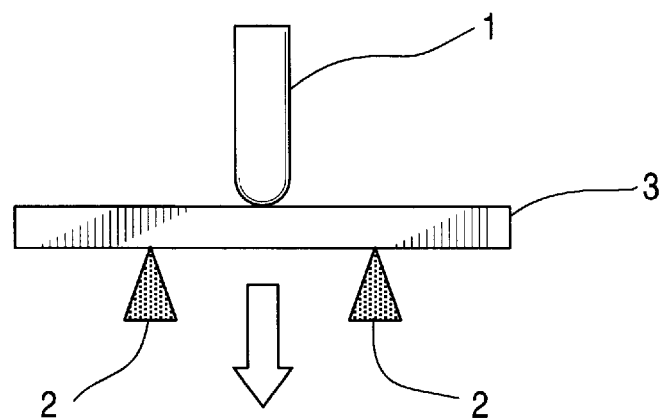
FIG. 1 illustrates the method of a three-point bending test.

The present invention has been made on the basis of the above findings (1) to (3), and the gist of the present invention is An integral intraocular lens having a haptic portion and an optic portion comprising an effective optic area surrounded by a peripheral portion, the optic portion and the haptic portion formed of a three-dimensionally crosslinked polymethyl methacrylate, wherein:

the three-dimensionally crosslinked polymethyl methacrylate constituting the effective optic area is a three-dimensionally crosslinked polymethyl methacrylate which is not soluble in an organic solvent such as benzene in which linear polymethyl methacrylate is soluble, and which is crosslinked to an extent that the three-dimensionally crosslinked polymethyl methacrylate swells in and has an organic solvent content of 45 to 70% when the three-dimensionally crosslinked polymethyl methacrylate is immersed in the organic solvent, the three-dimensionally crosslinked polymethyl methacrylate constituting the peripheral portion of the effective optic area and the haptic portion is obtained by press-stretching the same three-dimensionally crosslinked polymethyl methacrylate as the non-pressed three-dimensionally crosslinked polymethyl methacrylate constituting the effective optic area until the press-stretched three-dimensionally crosslinked polymethyl methacrylate has a compression ratio of 45 to 70%, and provided the difference between the organic solvent content of the three-dimensionally crosslinked polymethyl methacrylate constituting the effective optic area when immersed in said organic solvent and the compression ratio of the press-stretched three-dimensionally crosslinked polymethyl methacrylate constituting both the peripheral portion and the haptic portion is at most about 10%.

Another aspect of the present invention includes a

A flexible, one-piece intraocular lens made of three-dimensionally crosslinked polymethyl methacrylate durable to YAG laser irradiation, the lens having an effective optic area, a peripheral portion around the effective optic area and a haptic portion, wherein the three-dimensionally crosslinked polymethyl methacrylate constituting the effective optic area is a three-dimensionally crosslinked polymethyl methacrylate which is insoluble in an organic solvent such as benzene in which a linear polymethyl methacrylate is soluble, and which is crosslinked to an extent that the three-dimensionally crosslinked polymethyl methacrylate swells in and has an organic solvent content of 45 to 70% when the three-dimensionally crosslinked polymethyl methacrylate is immersed in the organic solvent, the three-dimensionally crosslinked polymethyl methacrylate constituting the peripheral portion of the effective optic area and the haptic portion is obtained by press-stretching the same three-dimensionally crosslinked polymethyl methacrylate as the non-pressed three-dimensionally crosslinked polymethyl methacrylate constituting the effective optic area until the press-stretched three-dimensionally crosslinked polymethyl methacrylate has a compression ratio of 45 to 70%, provided the difference between the organic solvent content of the three-dimensionally crosslinked polymethyl methacrylate constituting the effective optic area when immersed in the organic solvent and the compression ratio of the press-streched three-dimensionally crosslinked polymethyl methacrylate constituting both the peripheral portion and the haptic portion is at most about 10%.

Another embodiment of the present invention is a process for producing an integral intraocular lens having a haptic portion and an optic portion comprising an effective optic area surrounded by a peripheral portion, the optic portion and the haptic portion formed of a three-dimensionally crosslinked polymethyl methacrylate, which process comprises the steps of:

(a) polymerizing a monomer mixture containing 96 to 99.5 parts by weight of methyl methacrylate and 4 to 0.5 part by weight of a crosslinking agent, to obtain a three-dimensionally crosslinked polymethyl methacrylate material, (b) heating the three-dimensionally crosslinked polymethyl methacrylate material obtained in the step (a), and selectively press-stretching an area of the three-dimensionally crosslinked polymethyl methacrylate, with a press plate having a hole having a diameter equal to, or greater than, the diameter of the effective optic area and equal to, or smaller than, the outer diameter of the peripheral portion to produce a press-stretched portion and a non-press-stretched portion, the press-stretched portion having a thickness which is 55 to 30% of the thickness of the three-dimensionally crosslinked polymethyl methacrylate material which is not heated, the press-stretched portion having a compression ratio of 45 to 70%; and (c) forming an intraocular lens in which the effective optic area is a non-press-stretched portion corresponding to a position of the hole of the press plate and the peripheral portion and the haptic portion are made of the press-stretched portion which does not correspond to the position of the hole of the press plate.

EXAMPLES

The present invention will be explained with reference to Examples hereinafter.

Example 1

Example 1 used the following materials.

| | |
|---|---|
| Methyl methacrylate (MMA) | 98.1 parts by weight |
| Crosslinking agent, ethylene glycol dimethacrylate (EDMA) | 2.0 parts by weight |
| Polymerization initiator, azobisisobutyronitrile (AIBN) | 0.05 part by weight |
| UV absorbent, 2-(2'-hydroxy-3'-tert-butyl-5'-methylphenyl)-5-chlorobenzotriazole | 0.05 part by weight |
| Yellow dyestuff, C.I. (color index) Solvent Yellow 16 | 0.01 part by weight |

A monomer mixture of the above materials was polymerized in a polyethylene pipe having an inner diameter of 20 mm to obtain a three-dimensionally crosslinked PMMA material. Three cylindrical samples having a diameter of 16 mm and a thickness of 9 mm, 7 mm or 6 mm were taken from the above material. The samples were set in a compression molding machine and heated at 135° C., and the temperature of 135° C. was maintained for 15 minutes. Then, a press plate was lowered and preliminarily pressed on the cylindrical samples at a pressure of 2 kg/cm² twice. Further, the cylindrical samples were pressed with the press plate at a pressure of 25 kg/cm². In this case, a spacer formed of brass having a thickness of 3.5 mm was placed on a sample bed. Then, while the pressure of 25 kg/cm² was maintained, water was circulated in the compression molding machine to cool the samples to room temperature. Then, the pressure was released, the press plate was moved upward, and the press-stretched materials were taken out. When calculated on the basis of the following equation, the compression ratio (%) of the press-stretched materials were as follows.

Compression ratio = {[thickness of sample before compression (mm) − thickness of sample after compression (mm)]/[thickness of sample before compression (mm)]} × 100
(a) When the cylindrical sample having a thickness of 9 mm was press-stretched to a thickness of 3.5 mm:
  Compression ratio (%) = [(9.0 − 3.5)/(9.0)] × 100
  = 61(%)
(b) When the cylindrical sample having a thickness of 7 mm was press-stretched to a thickness of 3.5 mm:
  Compression ratio (%) = [(7.0 − 3.5)/(7.0)] × 100
  = 50(%)
(c) When the cylindrical sample having a thickness of 6 mm was press-stretched to a thickness of 3.5 mm:
  Compression ratio (%) = [(6.0 − 3.5)/(6.0)] × 100
  = 42(%)

As described above, three press-stretched three-dimensionally crosslinked PMMA materials having different compression ratios were obtained.

Example 2

Example 2 used the following materials.

| | |
|---|---|
| Methyl methacrylate (MMA) | 99.0 parts by weight |
| Crosslinking agent, ethylene glycol dimethacrylate (EDMA) | 1.0 part by weight |
| Polymerization initiator, azobisisobutyronitrile (AIBN) | 0.05 part by weight |
| UV absorbent, 2-(2'-hydroxy-3'-tert-butyl-5'-methylphenyl)-5-chlorobenzotrizole | 0.05 part by weight |
| Yellow dyestuff, C.I. (color index) Solvent Yellow 16 | 0.01 part by weight |

A three-dimensionally crosslinked PMMA material was obtained from a monomer mixture of the above materials under the same conditions as those in Example 1. Further, three press-stretched three-dimensionally crosslinked PMMA materials having different compression ratios were obtained under the same consitions as those in Example 1.

Comparative Example 1

Comparative Example 1 used the following materials. A monomer mixture in Comparative Example 1 differed from those in Examples 1 and 2 in that the monomer mixture in Comparative Example 1 did not contain the crosslinking agent.

| | |
|---|---|
| Methyl methacrylate (MMA) | 100.0 parts by weight |
| Polymerization initiator, azobisisobutyronitrile (AIBN) | 0.05 part by weight |
| UV absorbent, 2-(2'-hydroxy-3'-tert-butyl-5'-methylphenyl)-5-chlorobenzotriazole | 0.05 part by weight |
| Yellow dyestuff, C.I. (color index) Solvent Yellow 16 | 0.01 part by weight |

A three-dimensionally crosslinked PMMA material was obtained from a monomer mixture of the above materials under the same conditions as those in Example 1. Further, three press-stretched three-dimensionally crosslinked PMMA materials having different compression ratios were obtained under the same consitions as those in Example 1.

Comparative Example 2

Comparative Example 2 used the following materials. A monomer mixture in Comparative Example 2 differed from those in Examples 1 and 2 in that the monomer mixture in Comparative Example 2 contained a large amount, i.e., 4.0 parts by weight, of the crosslinking agent, larger than 2.0 parts by weight in Example 1 and 1.0 part by weight in Example 2.

| | |
|---|---|
| Methyl methacrylate (MMA) | 96.0 parts by weight |
| Crosslinking agent, ethylene glycol dimethacrylate (EDMA) | 4.0 part by weight |
| Polymerization initiator, azobisisobutyronitrile (AIBN) | 0.05 part by weight |
| UV absorbent, 2-(2'-hydroxy-3'-tert-butyl-5'-methylphenyl)-5-chlorobenzotriazole | 0.05 part by weight |
| Yellow dyestuff, C.I. (color index) Solvent Yellow 16 | 0.01 part by weight |

A three-dimensionally crosslinked PMMA material having a high crosslinking density was obtained from a monomer mixture of the above materials under the same conditions as those in Example 1. Further, three press-stretched three-dimensionally crosslinked PMMA materials having different compression ratios and having a high crosslinking density were obtained under the same consitions as those in Example 1.

The PMMA materials (before the pressing and stretching) obtained in Examples 1 and 2 and Comparative Examples 1 and 2, and the press-stretched PMMA materials obtained in Examples 1 and 2 and Comparative Examples 1 and 2 were tested as follows.

(1) Test of immersion in benzene

A disk-shaped plate having a thickness of 1 mm and a diameter of 16 mm was prepared from each of the PMMA materials (non-press-stretched) obtained in Examples 1 and 2 and Comparative Examples 1 and 2 by mechanical processing. The disk-shaped plate was weighed with an electronic balance and then placed in a sample bottle, and the sample bottle was charged with benzene and closed. The sample bottle was allowed to stand in an electric furnace of which the temperature was set at 40° C., for 24 hours, then taken out of the electric furnace, and cooled to room temperature, and the disk-shaped plate was visually observed. A plate which swelled uniformly was taken as "○", and a plate which was dissolved or so deformed as to lose its original shape was taken as "X".

Further, a plate which was not dissolved was taken out of the sample bottle after 240 hours, lightly swept on the surface and weighed with an electronic balance, and a solvent content was calculated on the basis of the following equation.

Solvent content (%) = {[sample weight (g) after immersion in solvent − sample weight (g) before immersion in solvent]/[sample weight (g) after immersion in solvent]} × 100

(3) Three-point bending test

A three-point bending test sample having a width of 1.5 mm, a height of 1.0 mm and a length of 18.0 mm was prepared from each of the PMMA materials and the press-stretched materials obtained in Examples 1 and 2 and Comparative Examples 1 and 2 by mechanical processing.

FIG. 1 illustrates the three-point bending test. A pressure wedge 1 had a radius of 1.25 mm, support beds 2 had a radius of 2.0 mm, an interflucrum distance was 10 mm, and a universal material tester supplied by Instron was used for the test. A sample 3 was placed on the support beds 2 and 2, and the a load was downwardly applied with the pressure wedge 1.

A bending strength (kgf/cm$^2$) was calculated on the basis of the following equation.

Bending strength=$(3 \times F \times L)/(2 \times b \times h^2)$

F: maximum load (kg)

L: interflucrum distance (=10 mm)

b: width (mm)

h: height (mm)

Concerning the amount (mm) of deflection at break, a deflection amount at a time when a sample was broken by pressing an indenter was determined on the basis of a movement distance (mm) of a cross head of the material tester.

Table 1 shows the results of the above two tests.

TABLE 1

| Ex. No. | Test of immersion of PMMA materials (non-press-stretched) | | Three-point bending test of press-stretched materials | | | | |
|---|---|---|---|---|---|---|---|
| | in benzene | | Items mea-sured | Compression ratio when materials were press-stretched | | | |
| | Appear-ance | Content (%) | | 0% | 42% | 50% | 61% |
| Ex. 1 | ○ | 51.4 | A* | 15.966 | 15.519 | 16.329 | 16.141 |
| | | | B* | 3.005 | 5.989 | 7.014 | 3.465 |
| Ex. 2 | ○ | 61.5 | A* | 14.986 | 15.457 | 15.538 | 16.121 |
| | | | B* | 2.646 | 6.085 | 6.517 | 7.121 |
| CEx. 1 | X | dissolv-ed | A* | 14.367 | 15.408 | 15.657 | 15.625 |
| | | | B* | 1.794 | 7.755 | 7.698 | 7.858 |
| CEx. 2 | X | 42.5 | A* | 15.301 | 15.797 | 15.860 | 15.292 |
| | | | B* | 2.727 | 4.049 | 3.359 | 1.763 |

Ex. = Example,
CEx. = Comparative Example
A*: Bending strength: kgf/mm$^2$,
B*: Amount of deflection at break: mm Table 1 shows the following.

In the benzene immersion test of the PMMA materials (non-press-stretched), the samples obtained in Examples 1 and 2 showed a uniform swelling in appearance since they had a moderate crosslinked structure, and they had solvent contents of 51.4% and 61.5%. On the other hand, the sample having no crosslinked structure, obtained in Comparative Example 1, was completely dissolved, and it was not measurable for a solvent content after immersed. Further, the sample having a crosslinked structure and having a high crosslinking desnity, obtained in Comparative Example 2, did not uniformly swell and underwent unregulated deformation, and numerous concave and convex portions were observed on its surface. The sample obtained in Comparative Example 2 had a solvent content of 42.2% after being immersed.

Concerning the three-point bending test of the press-stretched materials having a compression ratio of 0, 42, 50 or 60%, Table 1 shows bending strength data and amounts of deflection at break. The compression ratio of 0% means that samples prepared from polymers (materials) which were not press-stretched were used for the measurement. Table 1 shows that there are no great difference in bending strength among the samples obtained in Examples 1 and 2 and Comparative Examples 1 and 2. The reason therefor is as follows. In the process in which the sample was pressed with the indenter, the sample showed a maximum load of about 1.5 kg at a deflection amount of about 2.5 mm, and thereafter, the load was alleviated or decreased and continued to decrease even if the deflection amount increased. A major difference between the samples of Examples 1 and 2 and the samples of Comparative Examples 1 and 2 was found in amount of deflection at break. That is, a fragile material shows a small amount of deflection at break, and a material excellent in durability against breaking by bending shows a large amount of deflection at break. When the sample having a compression ratio of 0% (non-press-stretched) in Comparative Example 1 showed a small amount of deflection at break, while the value of the amount of deflection at break remarkably increased when the material was press-stretched at a compression ratio of 42, 50 or 61%. Further, the samples having compression ratios of 42, 50 and 61% showed almost constant amounts of deflection at break regardless of the compression ratios. This fact shows that a linear PMMA can be easily and reliably improved in mechanical strength by pressing and stretching it as has been conventionally known so that an integral intraocular lens which is almost free from breaking of the haptic portion can be obtained.

On the other hand, in the materials of three-dimensionally crosslinked PMMA, the amount of deflection at break greatly differed depending upon crosslinking densities and compression ratios employed for the pressing and stretching. In the samples having a high crosslinking density, obtained in Comparative Example 2, the samples were not improved in the amount of deflection at break, and moreover, the sample having a compression ratio of 61% showed a decrease in the amount of deflection at break. This fact clearly shows that it is difficult to improve a crosslinked material in strength by stretching it as has been considered. However, in the samples having a proper crosslinking degree and a relatively moderate crosslinking density, obtained in Examples 1 and 2, an improvement was found in the amount of deflection at break. In particular, the sample having a compression ratio of 50% from the material in Example 1 and the sample having a compression ratio of 61% from the material in Example 2 showed amounts of deflection at break almost similar to that of the sample obtained from the linear PMMA in Comparative Example 1. Further, in Example 1 in which the material had a smaller crosslinking density, the sample having a compression ratio of 50% showed a maximum value of amount of deflection at break, and in Example 2 in which the material had a greater crosslinking density than that in Example 1, the sample having a compression ratio of 61% showed a maximum value of amount of defection at break. This fact shows that it is required to select an optimum compression ratio depending upon crosslinking density.

As means for the above selection, the solvent content of the three-dimensionally crosslinked PMMA material (non-press-stretched) when it is uniformly swollen in an organic solvent and the compression ratio employed for press-stretching the three-dimensionally crosslinked PMMA material are brought into values close to each other. In the above Examples, the three-dimensionally crosslinked PMMA material (non-press-stretched) in Example 1 showed a solvent content of 51.4% after immersed in benzene, and the sample obtained by press-stretching the three-dimensionally crosslinked PMMA material at a compression ratio of 50% in Example 1 showed the largest amount of deflection at break in the three-point bending test. Further, the three-dimensionally crosslinked PMMA material (non-press-stretched) in Example 2 showed a solvent content of 61.5% after immersed in benzene, and the sample obtained by press-stretching the three-dimensionally crosslinked PMMA material at a compression ratio of 60% in Example 2 showed the largest amount of deflection at break in the three-point bending test.

That is, according to the finding of the present inventor, it is required to bring the solvent content (crosslinking density) of a three-dimensionally crosslinked PMMA material before compression treatment when immersed in a solvent and the compression ratio (press-stretching ratio) of the material after the compression treatment into values close to each other, for obtaining a three-dimensionally crosslinked PMMA material which has improved breaking durability equivalent to that of a material obtained by press-stretching a known linear PMMA.

Example 3

An intraocular lens was prepared by heating and press-stretching the three-dimensionally crosslinked PMMA material obtained in Example 1. The details thereof are as follows.

The three-dimensionally crosslinked PMMA material (which was to show a solvent content of 51% after immersion in benzene) obtained in Example 1 was processed into a cylindrical sample having a diameter of 16 mm and a thickness of 7 mm. A hole having a diameter of 5.5 mm was made in a press plate of a compression molding machine, and the cylindrical sample was placed on a sample bed of the compression molding machine such that the above hole was positioned in the center of the cylindrical sample. Then, the cylindrical sample was heat-treated and press-stretched under the same conditions as those in Example 1 except that the compression ratio was set at 50%.

The above-obtained press-stretched material was visually observed to show neither cracking nor damage, and no whitening was caused.

Further, the above press-stretched material was processed into a button for an integral intraocular lens, and in this case, the processing was smoothly carried out without causing any damage on the button for an integral intraocular lens.

Then, an integral intraocular lens having an effective optic area formed of a non-press-stretched portion and peripheral and haptic portions formed of a press-stretched portion was prepared from the above-obtained button, and the integral intraocular lens was evaluated for the following physical properties. As Referential Example, further, the three-dimensionally crosslinked PMMA material in Example 1 was processed into an integral intraocular lens without press-stretching it, and the obtained integral intraocular lens was similarly evaluated for physical properties.

Figure 2A:
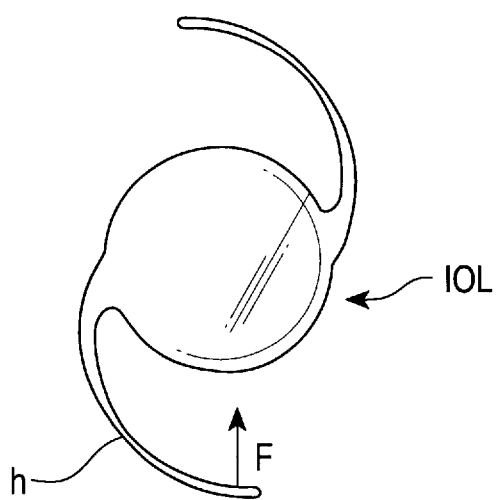
FIG. 2A is a plan view of a one-piece intraocular lens illustrating the method of tensile testing in which tension is applied at an angle of 30°.
Figure 2B:
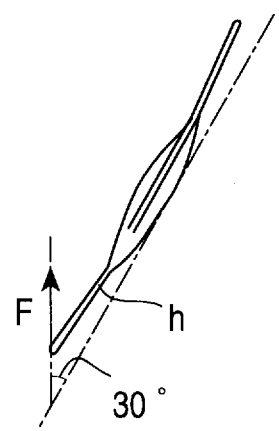
FIG. 2B is a side view of a one-piece intraocular lens illustrating the method of tensile testing in which tension is applied at an angle of 30°.

(1) Tests of strength of haptic portion (i) FIG. 2 shows the method of a tensile test in which a tension was applied in a direction at 30°. FIG. 2(A) shows a plan view of an intraocular lens, and FIG. 2 (B) shows a side view of the intraocular lens. As shown in FIG. 2(B), the intraocular lens to be tested was tilted at an angle of 30° against a vertical axis. The central portion of the haptic portion was held, and pulled upward along the vertical axis (in the direction indicated by an arrow in FIG. 2(A)) at a rate of 50 mm/min. And, a maximum load (g) when the haptic portion broke was determined.

(ii) Breaking test by press-bending

Figure 3:
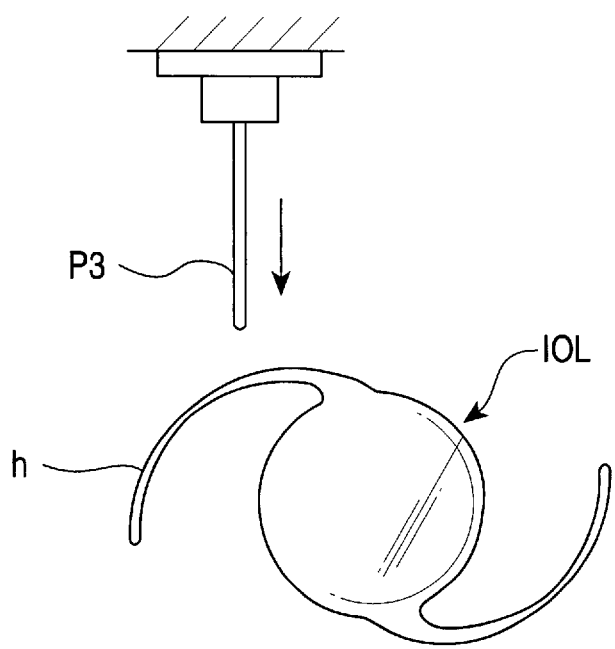
FIG. 3 illustrates the method of a breaking test by press-bending.

FIG. 3 shows the method of a breaking test by press-bending. In the braking test by press-bending, while the bottom of the haptic portion of the intraocular lens was compressed with a narrow and long compressing rod at a rate of 50 mm/minute, it was observed whether or not the haptic portion would break.

(2) Test of YAG laser durability

The optic portion of an integral intraocular lens was irradiated with YAG laser at different irradiation energy levels 10 times each. The irradiation energy levels were 2 mJ, 4 mJ and 7 mJ.

The irradiated lens was observed through a stereomicroscope (SZH, supplied by Olympus Optical Co., Ltd.) to determine an occurrence ratio (%) of pits and cracking.

Comparative Example 3

An intraocular lens was prepared by heating and press-stretching the linear crosslinked PMMA material obtained in Comparative Example 1. The details thereof are as follows.

The linear PMMA material (which was to be dissolved in benzene when immersed therein) obtained in Comparative Example 1 was processed into a cylindrical sample having a diameter of 16 mm and a thickness of 7 mm. A hole having a diameter of 5.5 mm was made in a press plate of a compression molding machine, and the cylindrical sample was placed on a sample bed of the compression molding machine such that the above hole was positioned in the center of the cylindrical sample. Then, the cylindrical sample was heat-treated and press-stretched under the same conditions as those in Example 1 except that the compression ratio was set at 50%.

Then, the above press-stretched material was processed into a button for an integral intraocular lens. Thereafter, an integral intraocular lens having an effective optic area formed of a non-press-stretched portion and peripheral and haptic portions formed of a press-stretched portion was prepared from the above-obtained button, and the integral intraocular lens was evaluated for physical properties in the same manner as above.

Table 2 shows the test results of the integral intraocular lens obtained in Example 3 and the test results of the intraocular lenses obtained in Comparative Example 3 and Referential Example.

TABLE 2

| Example No. | Test of strength of haptic portion | | YAG laser durability Occurrence ratio (%) of pits and cracking Irradiation energy | | |
|---|---|---|---|---|---|
| | Tension in direction 30° (g) | Breaking by press-bending | 2 mj | 4 mj | 7 mj |
| Intraocular lens obtained in Ex. 3 (press-stretched product) | 234.1 | Not broken | 0 | 0 | 10 |
| Intraocular lens obtained in Cex. 3 (press-stretched product) | 235.0 | Not broken | 10 | 30 | 60 |
| REx. (non-press-stretched product of Example 1) | 75.1 | Totally broken | 0 | 0 | 10 |

Ex. = Example,
CEx. = Comparative Example.
REx. = Referential Example

Table 2 shows the following. In Referential Example, the intraocular lens obtained directly from the three-dimensionally crosslinked PMMA material (non-press-stretched) of Example 1 without press-stretching it was formed of the three-dimensionally crosslinked PMMA material, and it was therefore excellent in YAG laser durability. However, it had fragility, the basic property of PMMA. In the tests of strength of the haptic portion, therefore, it was broken under a small load in the tensile test in a direction at 30°, and it was totally broken in the breaking test by press-bending.

In Comparative Example 3, the intraocular lens obtained from the material prepared by press-stretching the linear PMMA material of Comparative Example 1 at a compression ratio of 50% showed the occurrence of pits and cracking at high ratios, and was poor in YAG laser durability.

In Example 3, the intraocular lens obtained from the material prepared by press-stretching the three-dimensionally crosslinked PMMA material of Example 1 at a compression ratio of 50% showed press-stretching effects. In the tests of strength of the haptic portion, it showed a high strength in the tensile test in a direction at 30°, and no sample was broken in the breaking test by press-bending. In the test of YAG laser durability, further, almost no pit or cracking occurred in irradiated spots.

Other embodiments of the present invention not shown in the above Examples are as follows.

(1) In the intraocular lens obtained in Example 3, the effective optic area showed a solvent content of 51.4% when immersed in a solvent, and the haptic portion had a compression ratio of 50%, while the solvent content and the compression ration can be changed in the range of from 45 to 70%.

For accomplishing the effects of the present invention, however, it is essential to bring the solvent content of the effective optic area and the compression ratio of the haptic portion to values close to each other. A difference between the solvent content of the effective optic area portion and the compression ratio of the peripheral portion and the haptic portion is at most about 10%, particularly preferably in the range of from 0 to 10%. When the difference between the above two exceeds 10%, the breaking durability of the intraocular lens decreases.

(2) For producing three-dimensionally crosslinked PMMA, Example 1 used a mixture containing 98.0 parts by weight of methyl methacrylate and 2.0 parts by weight of a crosslinking agent, and Example 2 used a mixture containing 99.0 parts by weight of methyl methacrylate and 1.0 parts by weight of a crosslinking agent. However, the amount of methyl methacrylate can be set in the range of from 96 to 99.5 parts by weight, and the amount of the crosslinking agent can be set in the range of from 4 to 0.5 part by weight. When the amount of the crosslinking agent is less than 0.5 part by weight, the crosslinked structure is too moderate to work properly. That is, the resultant three-dimensionally crosslinked PMMA does not fully exhibit the functions such as YAG laser durability and physicochemical stability. When the amount of the crosslinking agent exceeds 4 parts by weight, the crosslinking density is too large, and it is difficult to press-stretch the resultant three-dimensionally crosslinked PMMA. Further, even if it is press-stretched, the mechanical strength does not increase, or the three-dimensionally crosslinked PMMA shows a decrease in mechanical strength in some cases.

(3) The following monomers may be used as required in combination with methyl methacrylate (MMA) used in Examples 1 and 2, for producing the three-dimensionally crosslinked PMMA. A methacrylate ester such as ethyl methacrylate, n-butyl methacrylate, iso-butyl methacrylate or tert-butyl methacrylate, and an acrylate ester such as methyl acrylate, ethyl acrylate, n-butyl acrylate, iso-butyl acrylate or tert-butyl acrylate. The following crosslinking agent maybe used in place of, or in combination with, the ethylene glycol dimethacrylate (EDMA) used in Examples 1 and 2. Diethylene glycol dimethacrylate, triethylene glycol dimethacrylate, tetraethylene glycol dimethacrylate or trimethylolpropane trimethacrylate.

(4) Examples 1 and 2 used azobisisobutyronitrile (AIBN) as a polymerization initiator, while the polymerization initiator may be selected from azobisdimethylvaleronitrile, benzoyl peroxide, di-tert-butyl peroxide or lauroyl peroxide.

(5) Besides the UV absorbent used in Examples 1 and 2, the UV absorbent may be selected from benzotriazole-containing absorbents such as 2(2'-hydroxy-5'-methylphenyl)benzotriazole, 2-(2'-hydroxy-5'-tert-butylphenyl)benzotriazole, 2-(2'-hydroxy-3,5'-di-tert-butylphenyl)benzotriazole, 2-(2'-hydroxy-3',5'-di-tert-butylphenyl)-5-chlorobenzotriazole, 2-(2'-hydroxy-3',5'-di-tert-amylphenyl)benzotriazole, and 2(2'-hydroxy-4'-octoxyphenyl)benzotriazole, salicylic acid-containing adsorbents such as phenyl salicylate, p-tert-butylphenyl salicylate and p-octylphenyl salicylate, and benzophenone-containing adsorbents such as 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfonebenzophenone.

(6) The yellow dyestuff may be selected from the following dyestuffs. CI (color index) Solvent Yellow 29, CI Solvent Yellow 33, CI Solvent Yellow 44, CI Solvent Yellow 56, CI Solvent Yellow 77, CI Solvent Yellow 93 and CI Disperse Yellow 3. Further, it may be also selected from yellowish brown colorants such as CI Solvent Yellow 14, CI Solvent Yellow 104, CI Solvent Yellow 105, CI Solvent Yellow 110, CI Solvent Yellow 112, CI Solvent Yellow 113 and CI Solvent Yellow 114.

(7) In Example 3, the press plate had a hole having a diameter (diameter of non-press-stretched portion) of 5.5 mm. However, the diameter of the hole of the press plate may be that which is equivalent to, or greater than, the diameter of the effective optic area and is equivalent to, or smaller than, the outer diameter of the peripheral portion to the above effective optic area. The effective optic area of a general intraocular lens has a diameter of 3 mm, and the total optic portion of the intraocular lens generally has a diameter (outer diameter of peripheral portion) of 5 mm to 7 mm. Therefore, the non-press-stretched portion has a diameter in the range of from 3 mm to 7 mm.

(8) In Example 3, the three-dimensionally crosslinked PMMA material was heated and press-stretched such that its thickness was decreased to 50% of the thickness of the material which was not heated. However, the thickness of the heated and press-stretched material can be properly set in the range of from 55 to 30% of the material which is not heated (corresponding to a compression ratio of 45 to 70%).

(9) In Example 3, the temperature for the heating and press-stretching was set at 135° C., while it is preferred to set the above temperature in the range of from 125° to 140° C. for improving the fluidity and processability of the three-dimensionally crosslinked PMMA material.

According to the present invention, there is provided an integral intraocular lens which is excellent in physicochemical stability and YAG laser durability and which has a haptic portion excellent in mechanical strength, by bringing the solvent content of the three-dimensionally crosslinked polymethyl methacrylate constituting the effective optic area when it is immersed in a solvent and the compression ratio of the three-dimensionally crosslinked polymethyl methacrylate constituting the haptic portion into predetermined ranges, and by bringing the solvent content of the effective optic area when it is immersed in a solvent and the compression ratio of the haptic portion into values close to each other.

Further, there is provided a method of producing an intraocular lens having the above advantages.

What is claimed is:

1. An integral intraocular lens having a haptic portion and an optic portion comprising an effective optic area surrounded by a peripheral portion, the optic portion and the haptic portion formed of a three-dimensionally crosslinked polymethyl methacrylate, wherein:
   the three-dimensionally crosslinked polymethyl methacrylate constituting the effective optic area is a three-dimensionally crosslinked polymethyl methacrylate which is not soluble in benzene an organic solvent, in which a linear polymethyl methacrylate is soluble, and which is crosslinked to an extent that the three-dimensionally crosslinked polymethyl methacrylate swells in and has benzene content of 45 to 70% when the three-dimensionally crosslinked polymethyl methacrylate is immersed in the benzene for 240 hours, the three-dimensionally crosslinked polymethyl methacrylate constituting the peripheral portion of the effective optic area and the haptic portion is obtained by press-stretching the same three-dimensionally crosslinked polymethyl methacrylate as a non-pressed three-dimensionally crosslinked polymethyl methacrylate constituting the effective optic area until the press-stretched three-dimensionally crosslinked polymethyl methacrylate has a compression ratio of 45 to 70%, and provided the difference between the benzene content of the three-dimensionally crosslinked polymethyl methacrylate constituting the effective optic area when immersed in said benzene and the compression ratio of the press-stretched three-dimensionally crosslinked polymethyl methacrylate constituting both the peripheral portion and the haptic portion is at most about 10%.

2. The intraocular lens of claim 1, wherein a difference between the benzene content of the effective optic area when the three-dimensionally crosslinked polymethyl methacrylate constituting the effective optic portion is immersed in the benzene and the compression ratio of the peripheral portion and the haptic portion is 0 to 10%.

3. The intraocular lens of claim 1 wherein the optic portion is durable to YAG laser irradiation.

4. A flexible, one-piece intraocular lens made of three-dimensionally crosslinked polymethyl methacrylate durable to YAG laser irradiation, said lens having an effective optic area, a peripheral portion around the effective optic area and a hepatic portion, wherein the three-dimensionally crosslinked polymethyl methacrylate constituting the effective optic area is a three-dimensionally crosslinked polymethyl methacrylate which is insoluble in benzene, an organic solvent in which a linear polymethyl methacrylate is soluble, and which is crosslinked to an extent that the three-dimensionally crosslinked polymethyl methacrylate swells in and has a benzene content of 45 to 70% when the three-dimensionally crosslinked polymethyl methacrylate is immersed in said benzene for 240 hours, the three-dimensionally crosslinked polymethyl methacrylate constituting the peripheral portion of the effective optic area and the haptic portion is obtained by press-stretching the same three-dimensionally crosslinked polymethyl methacrylate as a non-pressed three-dimensionally crosslinked polymethyl methacrylate constituting the effective optic area until the press-stretched three-dimensionally crosslinked polymethyl methacrylate has a compression ratio of 45 to 70%, provided the difference between the benzene content of the three-dimensionally crosslinked polymethyl methacrylate constituting the effective optic area when immersed in said benzene and the compression ratio of the press-stretched three-dimensionally crosslinked polymethyl methacrylate constituting both the peripheral portion and the haptic portion is at most about 10%.

* * * * *